United States Patent [19]

Tanihata

[11] Patent Number: 5,721,384
[45] Date of Patent: Feb. 24, 1998

[54] AUTOMATIC SAMPLER

[75] Inventor: Hiroshi Tanihata, Kyoto, Japan

[73] Assignee: Shimadzu Corporation, Japan

[21] Appl. No.: 696,273

[22] Filed: Aug. 13, 1996

[30] Foreign Application Priority Data

Sep. 29, 1995 [JP] Japan ..................... 7-276799

[51] Int. Cl.$^6$ ........................... G01N 21/01
[52] U.S. Cl. ........................... 73/864.81
[58] Field of Search ............ 73/864.21, 864.23–864.25,
73/864.31, 864.81; 422/63; 414/226, 744.2,
744.3, 744.6, 744.8; 901/46, 47, 32

[56] References Cited

U.S. PATENT DOCUMENTS

| | | |
|---|---|---|
| 1,211,611 | 1/1917 | Meyer et al. ............ 414/744.3 |
| 4,057,148 | 11/1977 | Meyer et al. |
| 5,207,554 | 5/1993 | Asakawa et al. ............ 414/744.6 |
| 5,411,065 | 5/1995 | Meador et al. |
| 5,525,298 | 6/1996 | Anami ............ 422/63 |

*Primary Examiner*—Robert Raevis
*Attorney, Agent, or Firm*—Majestic, Parsons, Siebert & Hsue P.C.

[57] ABSTRACT

An automatic sampler has a robot arm capable of moving linearly and/or rotationally in a plurality of directions. A pair of gripper plates, attached to the robot arm, can be driven towards or away from each other such that vials of different sizes can be gripped between them. Vials of different sizes are carried on a plurality of trays each provided with slits representing the size of vials carried on it. Motions of both the drivers for moving the robot arm in these different directions and the gripper plates towards or away from each other are controlled by a central processing unit.

5 Claims, 2 Drawing Sheets

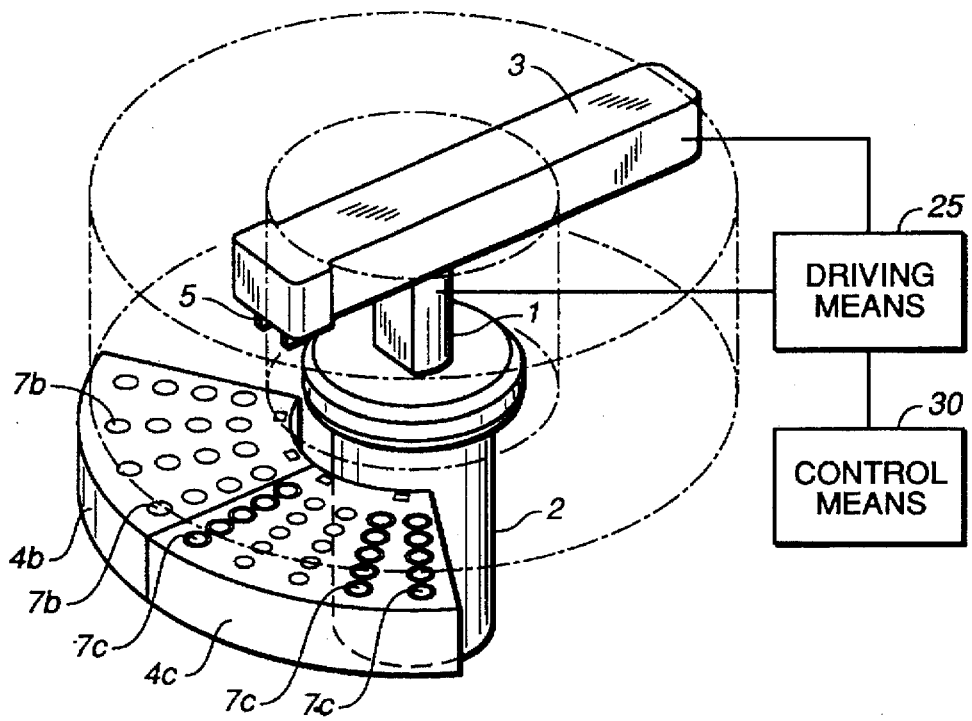
FIG._1
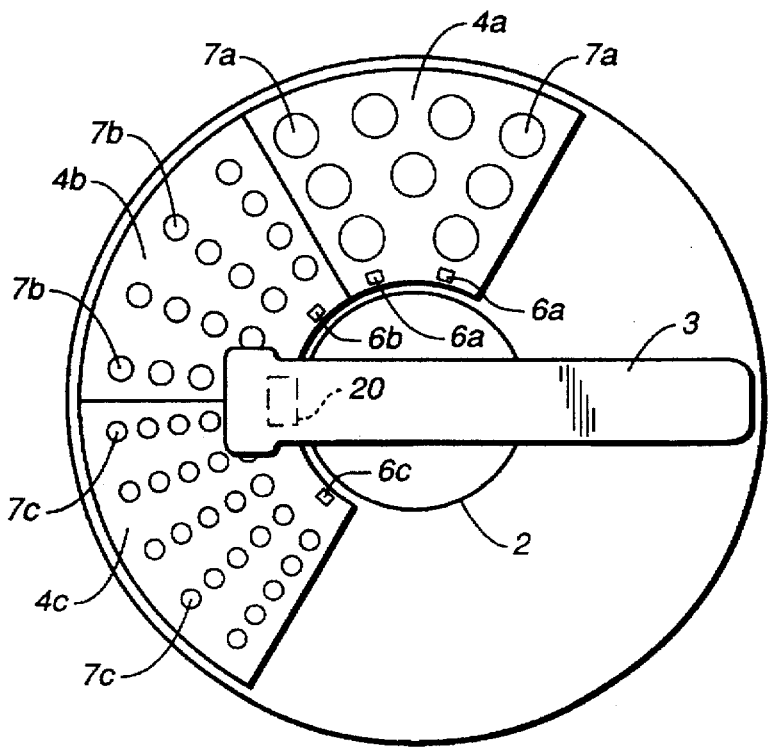
FIG._2

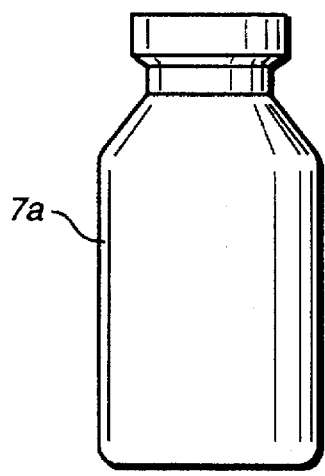
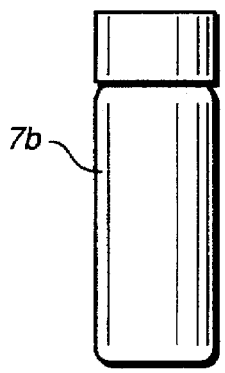
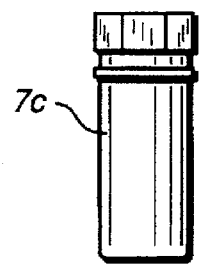
FIG._3A     FIG._3B     FIG._3C
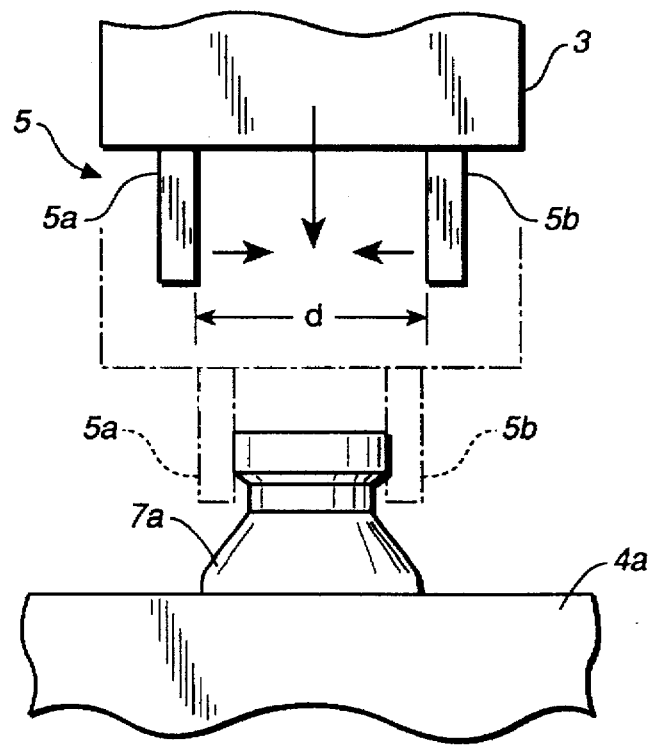
FIG._4

5,721,384

1

AUTOMATIC SAMPLER

BACKGROUND OF THE INVENTION

This invention relates to an automatic sampler, or an auto-sampler, used when samples are analyzed by an analyzer such as a gas chromatograph, a liquid chromatograph or a spectroscopic analyzer. In particular, this invention relates to such an auto-sampler capable of smoothly handling sample-containing vials of different sizes.

When samples are analyzed by an analyzer such as a gas chromatograph, samples are normally placed in vials of a same size and processes such as extraction, condensation, clean-up (or removal of impurities), addition of a reagent and stirring are carried out before they are used for an quantitative analysis. Since prior art auto-samplers are adapted to handle vials of a same size, not only are vials of the same size used for all processes from the pre-treatment to the introduction to an analyzer such as a gas chromatograph, but also handling apparatus particularly designed for handling vials of that size are set for holding and lifting the vials. For using vials of different sizes, it has been known to replace a removably attachable hand grip on the sampler.

In other words, although vials of different sizes are available, each suited for different one of the processes to be carried out such as sample extraction, condensation and clean-up, prior art auto-samplers carry out all these pre-treatment processes by using vials of a same size. It now goes without saying that this adversely affects the efficiency of the auto-sampler. Moreover, the use of a removably attachable hand grip makes it difficult to automate the processes because neither the pre-treatment nor the analysis can be carried out unless the sizes of the hand grip and the vials match. In particular, an auto-sampler with a hand grip designed only for one size of vials cannot function when a pre-treatment unit contains vials of different sizes.

SUMMARY OF THE INVENTION

It is therefore an object of this invention to provide an improved auto-sampler capable of handling vials of different sizes with a single hand grip even if such vials of different sizes are mixed.

An auto-sampler embodying this invention, with which the above and other objects can be accomplished, may be characterized as comprising a robot arm capable of moving in a plurality of directions (inclusive of rotational directions), driving means for causing the robot arm to move (linearly and/or rotationally) in these directions, gripping means attached to the robot arm for gripping vials of different sizes, a plurality of trays each containing vials of a different size, identifying means for identifying the trays such as slits made in the trays and a photo-sensor for detecting these slits, and control means such as a central processing unit for controlling the operations of the driving means and the gripping means.

BRIEF DESCRIPTION OF THE DRAWINGS

The accompanying drawings, which are incorporated in and form a part of this specification, illustrate embodiments of the invention and, together with the description, serve to explain the principles of the invention. In the drawings:

FIG. 1 is a diagonal external view of an auto-sampler embodying this invention with its driving control means schematically indicated as a block diagram;

FIG. 2 is a plan view of the auto-sampler of FIG. 1;

2

FIGS. 3A, 3B and 3C are external views of vials of different sizes which can be picked up by the auto-sampler of FIG. 1; and FIG. 4 is a side view of the hand grip of the auto-sampler of FIG. 1.

DETAILED DESCRIPTION OF THE INVENTION

As shown in FIG. 1, an auto-sampler according to this invention has a shaft 1 inserted into a case 2 containing therein a driving mechanism using a DC motor and gears such that the shaft 1 can rotate around its own axis. A horizontally elongated member, referred to as the robot arm 3, of a detachable type is attached to the top of the shaft 1. The robot arm 3 is slidable horizontally, for example, along a rail and a guide (not shown) by means of a pinion (not shown) driven by a driving mechanism inside the shaft 1 itself and a rack gear (not shown) which is contained inside the arm 3 and engages with the pinion. The shaft 1 is also movable vertically upward and downward by means of a vertically driving mechanism (not shown) therefor. In other words, the end position of the robot arm 3 can be described most conveniently by a cylindrical coordinate system R (horizontal radial direction), Θ (rotational direction around a vertical axis) and Z (vertical direction).

A hand grip 5, serving as vial holding means, is provided at an end of the robot arm 3 on the downwardly oriented surface such that vials of different sizes can be gripped and supported thereby. In other words, there are four independently controllable motions involved in this auto-sampler, and each independently controlled motion is effected by a separate DC motor (all these motors being collectively indicated by numeral 25 as indicating a driving means) with the traveled distance detected by an encoder (not shown). The detected distances are inputted to a central processing unit CPU (serving as the control means 30) for control of various kinds.

As shown both in FIGS. 1 and 2, partitioned trays 4a, 4b, . . . , each containing vials 7a, 7b, . . . of different sizes, are disposed removably around the case 2. In other words, vials 7a, 7b, 7c of different sizes are made available as shown in FIGS. 3A, 3B, 3C because the amount of each sample to be analyzed will vary, depending upon the purpose of the analysis and the method of processing. FIGS. 1 and 2 show six trays 4a, 4b, . . . each subtending an angle of 60° at the center, but this is not intended to limit the scope of the invention. The number of partitions may be increased or decreased. Various devices and apparatus such as pretreatment devices including an extraction device, a condensation device and an impurity-removing device or a device for introducing samples into a gas chromatograph or a liquid chromatograph may be disposed along the outer peripheries of these trays 4a, 4b, . . . .

The trays 4a, 4b, . . . are provided with slits 6a, 6b, . . . , respectively, as shown in FIG. 2, serving as indicators of the size of the vials carried thereon. Thus, these slits may be replaced by bar codes or indicators of another kind. A photo-sensor 20 is provided to the robot arm 3 for detecting the slits 6a, 6b, . . . such that the shaft 1 can be rotated so as to allow the photo-sensor 20 to detect the slits 6a, 6b, . . . and thereby to learn vials of what size are contained in which of the trays 4a, 4b, . . . . According to a preferred embodiment, each of the trays 4a, 4b, . . . has at least two slits 6a, 6b, . . . at different angular positions and, when one of the trays 4a, 4b, . . . is specified, the CPU 30 serves to determine from known positions of these slits 6a, 6b, . . .

which one of the slits in the specified tray can be reached and examined by the photo-sensor 20 by rotating the robot arm 3 by the smallest angle, as well as the direction in which the robot arm 3 should be rotated for the purpose.

As shown in FIG. 4, the hand grip 5 attached to the robot arm 3 is comprised of a pair of gripper plates 5a, 5b adapted to move in the right-left direction (with respect to FIG. 4) towards or away from each other by means of a driving mechanism (shown schematically at 25 in FIG. 1) such that these gripper plates 5a, 5b can be caused to grip the head of a vial to be picked up (as indicated by broken lines in FIG. 4). In other words, the distance d between the gripper plates 5a, 5b is initially kept larger than the head size of the vial to be picked up and is thereafter reduced such that the head of the target vial can be securely gripped. The initial distance d between the gripper plates 5a, 5b must be selected such that those vials which are adjacent to the target vial to be picked up should not come into contact with either of the gripper plates 5a, 5b.

When a specified vial containing a sample is to be processed by an auto-sample thus structured, the CPU 30 effects the control as follows:

(1) When power is switched on or the auto-sampler has been reset (such as when trays have been replaced), the robot arm 3 is moved horizontally such that the slits 6a, 6b, ... in the trays 4a, 4b, ... can be detected by the photo-sensor 20, and the robot arm 3 is then rotated horizontally to determine which trays 4a, 4b, ... support vials of which size;

(2) When a process-start signal is received, the robot arm 3 is rotated and/or moved horizontally to the position of the specified vial to be processed, the hand grip 5 is controlled such that the distance d between the gripper plates 5a, 5b will be adjusted according to the size of (the head of) the specified vial to be picked up, and the shaft 1 is lowered;

(3) After the specified vial is gripped between the pair of gripper plates 5a, 5b on the specified tray, the robot arm 3 is lifted, rotated by a specified angle and moved horizontally to the specified destination (where is the apparatus to which the vial is to be transported) and lowered, and the vial is released; and (4) The steps (1)–(3) are repeated.

The invention has been described above by way of only one example but this example is not intended to limit the scope of this invention. Many modifications and variations are possible within the scope of the invention. For example, the position of the hand grip 5 at one end of the robot arm 3 need not be changed by individually varying coordinates of a cylindrical coordinate system, but a driving system may be set so that the hand grip 5 can move along mutually perpendicular axes of a rectilinear (XYZ) coordinates system. Thus, when the robot arm 3 is herein said to be movable in a plurality of directions, it is to be understood that rotational, as well as linear, directions of motion are included. In summary, auto-samplers according to this invention is capable not only of handling vials of different sizes without exchanging the hand grip but also of determining where to find a vial of what size. All such modifications and variations that may be apparent to a person skilled in the art are thus intended to be within the scope of the invention.

What is claimed is:

1. An automatic sampler comprising:

a robot arm capable of moving in a plurality of directions;

driving means for causing said robot arm to move in said plurality of directions;

gripping means attached to said robot arm for gripping vials of different sizes;

a plurality of trays each carrying thereon vials of a different size;

identifying means for identifying said plurality of trays and thereby the size of vials thereon; and control means for controlling said driving means and said gripping means.

2. The automatic sampler of claim 1 wherein said gripping means comprises a pair of gripper plates adapted to move towards and away from each other according to the size of a vial to be gripped.

3. The automatic sampler of claim 1 wherein said directions include vertical direction and rotation around a vertical axis.

4. The automatic sampler of claim 1 wherein said identifying means include slits formed in said trays and a photo-sensor attached to said robot arm for detecting said slits.

5. The automatic sampler of claim 1 wherein said robot arm is capable of rotating horizontally around a vertical axis selectively in either sense, said identifying means include at least two slits formed at different angular positions with respect to said vertical axis in each of said trays, and said control means determines the sense of rotation of said robot arm such that the angle of rotation by said robot arm is the least for causing said photo-sensor to reach and detect one of said slits in a specified one of said trays.

\* \* \* \* \*